United States Patent
Mans et al.

(10) Patent No.: US 6,235,302 B1
(45) Date of Patent: May 22, 2001

(54) BIOCIDE IMPREGNATED FIBER-REINFORCED SPONGE MATERIAL

(75) Inventors: Leo Mans; Klaus-Dieter Hammer, both of Mainz (DE)

(73) Assignee: Kalle Nalo GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/269,637

(22) PCT Filed: Sep. 6, 1997

(86) PCT No.: PCT/EP97/04849

§ 371 Date: Mar. 31, 1999

§ 102(e) Date: Mar. 31, 1999

(87) PCT Pub. No.: WO98/17165

PCT Pub. Date: Apr. 30, 1998

(30) Foreign Application Priority Data

Oct. 18, 1996 (DE) .......................................... 296 18 058 U

(51) Int. Cl.[7] .............................. A01N 25/34; A61K 9/70; A61K 9/52

(52) U.S. Cl. .................. 424/411; 424/404; 424/405; 424/409; 424/410; 424/413; 424/443; 424/457; 523/122

(58) Field of Search ................................... 424/404, 405, 424/409, 410, 413, 488, 443, 457; 523/122

(56) References Cited

U.S. PATENT DOCUMENTS

| 4,311,479 | 1/1982 | Fenn et al. ................................. 8/495 |
| 4,675,347 | 6/1987 | Mochizuki et al. .................. 523/122 |
| 4,940,631 | * 7/1990 | Colin et al. ........................ 428/309.9 |
| 5,441,742 | 8/1995 | Autant et al. ......................... 424/405 |

FOREIGN PATENT DOCUMENTS

| 12 97 852 | 6/1969 | (DE) . |
| 28 41 749 | 4/1979 | (DE) . |
| 28 34 914 | 2/1980 | (DE) . |
| 887 430 | 1/1962 | (GB) . |
| 2-153723 | 6/1990 | (JP) . |
| 2-160843 | 6/1990 | (JP) . |

* cited by examiner

*Primary Examiner*—Floyd D. Higel
*Assistant Examiner*—Ebenezer Sackey
(74) *Attorney, Agent, or Firm*—Foley & Lardner

(57) ABSTRACT

The present invention relates to a regenerated cellulose based sponge material with an inner viscose fiber reinforcement having a staple fiber length of 5-50 mm and impregnated with a biocide agent. Also disclosed is a regenerated cellulose based sponge material with an inner cotton fiber reinforcement having a staple fiber length of 5-50 mm and impregnated with a biocide agent. The coagulation and regeneration takes place in a bath that has a pH of 13 or higher and which includes Glauber's salt, NaOH and water.

15 Claims, No Drawings

BIOCIDE IMPREGNATED FIBER-REINFORCED SPONGE MATERIAL

This application is a 371 of PCT/EP97/04849 filed Sep. 6, 1997.

The present invention relates to a fiber-reinforced sponge cloth which is produced by the viscose process and which makes a versatile cleaning and decontaminating cloth, especially for the private household.

Sponge cloth production by the viscose process is well known. First, pulp, especially wood pulp, is converted with sodium hydroxide and carbon disulfide into an alkaline cellulose xanthate solution, so-called viscose solution. At the same time, cotton noils are degreased with dilute, detergent-containing NaOH and mercerized. Viscose solution and cotton fibers are then mixed together to form a homogeneous mass, generally with the aid of a kneader. Glauber's salt (sodium sulfate decahydrate) is then added and likewise mixed in uniformly. This sponge cloth raw material is then applied to a foraminous endless belt to whichever depth is desired. The regeneration of the cellulose then takes place in a heated, alkaline coagulation bath. It can also be carried out in an acidic medium, for example dilute sulfuric acid. In the process, the internal reinforcement becomes integrated into the sponge cloth body.

Glauber's salt has a very low melting point (about 32 to 33° C). It therefore melts in the coagulation bath and is dissolved out. The disappearing salt crystals leave pores and voids behind. Finally, the sponge cloth is washed out to rid it of salt residues and adhering reaction products. After drying, it is cut into narrow lengths, which in turn are rolled up. The roll material can then be end-itemed into cloths of the desired size. If desired, it can additionally be printed beforehand.

However, fibre-reinforced sponge cloths are brittle in the dry state. They are therefore marketed in this form only in a few countries. Moistened sponge cloths, in contrast, are more flexible and have a significantly better "hand". To keep the sponge cloth moist, the sponge cloth lengths are impregnated with the solution of a hygroscopic salt, especially magnesium chloride. Excess liquid is removed with the aid of a pair of squeeze rolls. The moist cloths are then packaged, normally in a polymeric film However, inside the package, micro-organisms, especially bacteria and fungi, can multiply, which shows itself in the form of dark spots on the sponge cloths.

It is an object of the present invention to kill these microorganisms or at least inhibit their propagation.

We have found that this object is achieved by a sponge cloth which is based on regenerated cellulose and has been provided with an internal reinforcement, wherefor the coagulation and regeneration takes place in a bath which has a pH of 13 of higher and which consists of Glauber's salt, NaOH and water and wherein the internal reinforcement consists of viscose fibres having a staple fibre length of 5 to 50 mm and which sponge cloth has been impregnated with a biocidally active agent. Viscose fibres are obtainable in a substantially more uniform quality than the hitherto customary cotton fibres. In addition, the ginning of cotton fibres does not succeed in removing all the seeds and trash. This impurity is particularly conspicuous in the case of undyed or light-colored sponge cloths. The seeds are visible therein as small black spots. It is true that the seeds are removable, but this is relatively costly. In addition, the color of natural cotton fibres is subject to fluctuations. Finally, cotton fibres have the disadvantage that they have to be degreased beforehand. Residues of the degreasing surfactants used tend to cause problems, especially due to foaming, in the production of the sponge cloth. It was further known that biocidally active quaternary ammonium salts, specifically benzalkonium chlorides, lose their efficacy in the presence of cotton fibres (Martindale, The Extra Pharmacopoeia, 28th ed., London [1982], page 549).

Preferred biocidally active agents for the purposes of the present invention are isothiazolone, benzisothiazolone and benzimidazole derivatives, especially those of the following formulae 1 to 12:

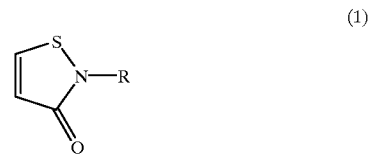
(1)

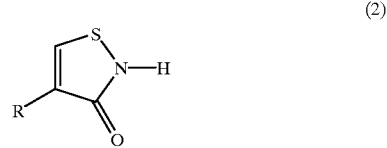
(2)

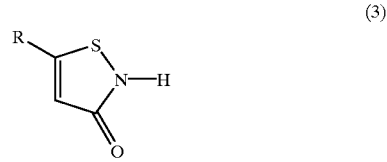
(3)

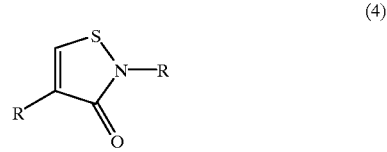
(4)

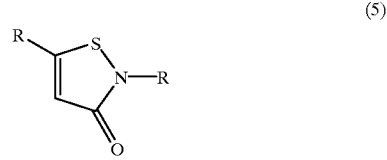
(5)

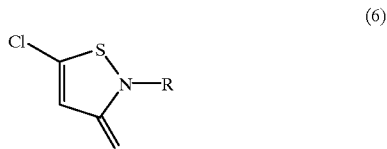
(6)

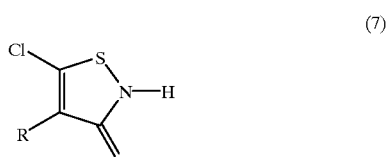
(7)

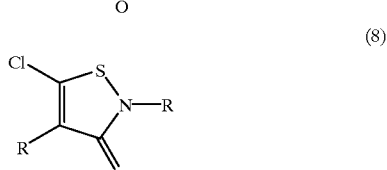
(8)

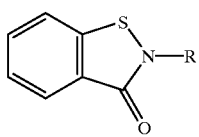

(9)

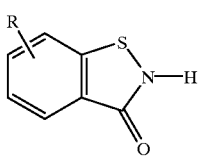

(10)

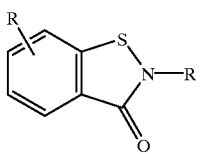

(11)

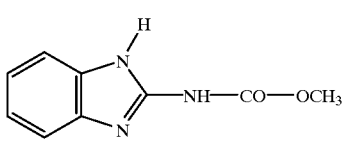

(12)

In the aforementioned formulae, R is an alkyl, alkenyl or alkadienyl radical, which generally comprises 1 to 20 carbon atoms and is preferably straight-chain. Of these, the straight-chain alkyl radicals having 6 to 18 carbon atoms are particularly preferred. The largest practicable N-alkyl radical is stearyl. Compounds whose N-alkyl radical comprises 14 carbon atoms or fewer generally have higher bactericidal effect. However, as the chain length decreases, the solubility in water increases. When more than one alkyl group is present, the total number of carbon atoms present therein is preferably likewise not more than 20. In the compound of the formula 7, R may also be a chlorine atom. In the chlorine-substituted isothiazolones, i.e., compounds 6 to 8, the alkyl group generally comprises only 1 to 12, preferably even only 1 to 8, carbon atoms. The second chlorine substituent enhances the bactericidal effect of the compound and, what is more, reduces its solubility in water. In the compounds of the formulae 9, 10 and 11, the alkyl radical is generally shorter. It contains only 1 to 4 carbon atoms, and methyl, ethyl and propyl radicals are preferred in turn.

In addition, R can also be a cycloalkyl radical which generally comprises 3 to 12 carbon atoms. In the chlorine-substituted isothiazolone compounds of the formulae 6 to 8, the cycloalkyl radical generally comprises only 3 to 8 carbon atoms, and the cyclohexyl radical is particularly noteworthy. Particular preference is given to the compounds of the formulae 1, 3, 6 and 9. The compound of the formula 12 (2-methoxycarbonylaminobenzimidazole) is also known under the INN name of carbendazim. Also suitable are, furthermore, 1-butylcarbamoyl-2-methoxycarbonylaminobenzimidazole (benomyl), 2-thiazol-4-ylbenzimidazole (thiobendazole) and 2-furan-2-ylbenzimidazole (fuberidazole).

Fungicidal and/or bactericidal action is also exhibited by quaternary ammonium salts having long-chain, generally saturated, but also unsaturated, alkyl groups having 6 to 24, preferably 10 to 18, carbon atoms. Of these cationic, surface-active ammonium salts, particularly suitable ones are di($C_{10}$–$C_{18}$)alkyl-dimethylammonium chlorides (such as didecyldimethylammonium chloride), ($C_8$–$C_{18}$) alkyltrimethylammonium chlorides (such as trimethyloctylammonium chloride, decyltrimethylammonium chloride and hexadecyltrimethylammonium chloride), soyalkyltrimethylammonium chloride, dicocalkyldimethylammonium chloride, alkyl-benzyldimethylammonium chlorides (such as benzyldimethylstearylammonium chloride, benzylcocalkyldimethylammonium chloride or cocalkyl(2,4-dichlorobenzyl)dimethylammonium chloride. Frequently, mixtures of quaternary ammonium salts of fatty acids of different lengths are used (cocalkyl and soyalkyl each represent a mixture of saturated or unsaturated alkyl groups of varying length). The anion in the ammonium salts need not necessarily be chloride. The anion may equally well be bromide, acetate, propionate, sorbate, benzoate or sulfate. These compounds are described in EP-A 286 009, for example.

The present invention finally also provides a sponge cloth which is based on regenerated cellulose and has been provided with an internal reinforcement, wherefore coagulation and regeneration takes place in a bath which has a pH of 13 or higher and which consists of Glauber's salt, NaOH and water and wherein the internal reinforcement consists of cotton fibres having a staple fibre length of 5 to 50 mm and which sponge cloth has been impregnated with a bactericidally active agent.

The bactericidally active agent therein is preferably one of the isothiazolone, benzisothiazolone or benzimidazole derivatives already mentioned.

The bactericidal agents used in the sponge cloth of the invention may also be dipyridyl disulfide and its bis-N-oxide, specifically dipyridin-2-yl disulfide. It is further possible to use the 1-alkyl- and 1-alkenyl-pyridinium salts (such as 1-laurylpyridinium chloride) likewise described in EP-A 286 009. It is also possible to use biguanide compounds as described in U.S. Pat. No. 4 675 347. Also suitable are penicillins, cephalosporins, tetracyclins and other antibacterially active compounds, provided they are officially approved for this purpose. Finally, it is also possible to combine a plurality of the aforementioned agents.

The biocidal impregnation may also be brought about by treating with glycerol or 1,2-propanediol (propylene glycol). To be effective, they have to be present in the sponge cloth in an amount which is sufficient to reduce the water activity (the so-called $a_w$ value) to 0.9 or less. An $a_w$ value of 0.85 or less will even inhibit the development of mold fungi (see E. Lück, Z Lebensm. Unters.-Forsch. 153 [1973] 42–52). Many of the compounds mentioned are active not only against fungi and bacteria, but also against yeasts, algae and other microorganisms.

The weight proportion attributable to the biocidally active compound(s) depends on the species of microorganisms and the constitution of the respective compound. In the case of a ($C_{12}$–$C_{18}$)alkylbenzyldimethylammonium chloride, the fungicidally effective amount is about 1100 to 1600 ppm, based on the dry weight of the sponge cloth. In the case of didecyldimethylammonium chloride, 1 ppm is sufficient for an algicidal effect.

The biocidally active agent can be added to the moistening bath mentioned. The bath preferably contains a magnesium chloride solution about 2 to 8% by weight in strength, especially about 4% by weight in strength. This production process is particularly favorable with regard to equipment. However, it may also be added to a separate treatment bath. The moistened sponge cloths contain about 0.01 to 0.4% by weight, preferably about 0.03 to 0.25% by weight, of $MgCl_2$, based on the dry weight of the sponge cloth. The impregnation with the hygroscopic salt and the impregnation with the biocidally active compound, however, are in principle independent of each other. Thus, even nonmoistened sponge cloths can be antibacterial.

The cotton or viscose fibers serving as internal reinforcement in the sponge cloth of the present invention preferably have a staple fiber length of 10 to 30 mm. The cotton fibers, as mentioned at the beginning, are degreased and optionally mercerized before use. The proportion of the dry weight of the sponge cloth attributable to the internal reinforcement is generally about 5 to 50% by weight, preferably 10 to 40% by weight.

The rest of the production process then preferably takes the form, described at the beginning, of kneading the cotton or viscose fibers with the viscose solution and subsequently also with Glauber's salt, spreading the mass obtained from the kneader onto a conveyor belt, coagulating by heating, washing and drying. The coagulation bath generally contains sodium hydroxide and is consequently strongly alkaline (pH $\geq$13). Instead of an alkaline coagulation bath, it is also possible to use an acidic bath having a pH of about 1. It customarily contains dilute sulfuric acid. In addition, the coagulation bath will usually also contain Glauber's salt.

We claim:

1. A sponge cloth which is based on regenerated cellulose and has been provided with an internal reinforcement consisting of viscose fibers having a staple fiber length of 5 to 50 mm, said sponge cloth being obtained by a process comprising the steps of coagulating and regenerating the cellulose in a bath which has a pH of 13 or higher and which comprises Glauber's salt, NaOH and water, and impregnating the sponge cloth with a biocidally active agent.

2. The sponge cloth of claim 1, wherein biocidally active agent is an isothiazolone, benzisothiazolone or benzimidazole compound.

3. The sponge cloth of claim 1, wherein the biocidally active agent is a quaternary ammonium salt.

4. The sponge cloth of claim 1, wherein the biocidally active agent is glycerol or 1,2-propanediol.

5. The sponge cloth of claim 1, wherein the staple fiber length of the viscose fibers is 10 to 30 mm.

6. The sponge cloth of claim 1, wherein the proportion of the dry weight of the sponge cloth attributable to the internal reinforcement is 5 to 50% by weight.

7. The sponge cloth of claim 1, moistened with an aqueous magnesium chloride solution.

8. A sponge cloth which is based on regenerate cellulose and has been provide with an internal reinforcement consisting of cotton fibers having a staple fiber length of 5 to 50 mm, said sponge cloth being obtained by a process comprising the steps of coagulating and regenerating the cellulose in a bath which has a pH of 13 or higher and which comprises Glauber's salt, NaOH and water, and impregnating the sponge cloth with a biocidally active agent.

9. The sponge cloth of claim 8, wherein the bactericidally active agent is an isothiazolone, benzisothiazolone or benzimidazole compound.

10. The sponge cloth of claim 8, wherein the staple fiber length of the cotton fibers is 10 to 30 mm.

11. The sponge cloth of claim 8, wherein the bactericidally active agent is a penicillin, cephalosporin, tetracyclin, a pyridinium salt or a biguanide compound.

12. The sponge cloth of claim 8, wherein the proportion of the dry weight of the sponge cloth attributable to the internal reinforcement is 5 to 50% by weight.

13. The sponge cloth of claim 8, moistened with an aqueous magnesium chloride solution.

14. The sponge cloth of claim 1, wherein the bactericidally active agent is applied subsequent to the regeneration of the cellulose.

15. The sponge cloth of claim 8, wherein the bactericidally active agent is applied subsequent to the regeneration of the cellulose.

* * * * *